US006037340A

United States Patent [19]
Castelhano et al.

[11] Patent Number: 6,037,340
[45] Date of Patent: Mar. 14, 2000

[54] SYNTHESIS AND USE OF THIOPHENE- AND PYRROLE-BASED HETEROAROMATIC COMPOUNDS

[75] Inventors: Arlindo L. Castelhano, New City; Bryan McKibben, White Plains, both of N.Y.

[73] Assignee: Cadus Pharmaceutical Corporation, Tarrytown, N.Y.

[21] Appl. No.: 08/864,240

[22] Filed: May 28, 1997

[51] Int. Cl.[7] .......................... A61K 31/38; A61K 31/40; A61K 31/435; C07D 205/02
[52] U.S. Cl. .......................... 514/183; 514/342; 514/422; 514/443; 514/447; 540/480; 540/596; 546/280.4; 548/527; 548/950; 548/962; 549/50; 549/68; 549/69
[58] Field of Search ................................... 514/443, 447; 549/68, 69, 50

[56] References Cited

U.S. PATENT DOCUMENTS

| | | | |
|---|---|---|---|
| 1,642,462 | 9/1927 | Reach | 473/290 |
| 3,732,212 | 5/1973 | Carabateas | 260/239.3 |
| 3,904,603 | 9/1975 | Kim | 260/239 |
| 3,925,361 | 12/1975 | Kim | 260/239 |
| 3,947,408 | 3/1976 | Wright, Jr. | 260/239.3 |
| 3,984,103 | 10/1976 | Nix | 473/291 |
| 4,147,349 | 4/1979 | Jeghers | 473/291 |
| 4,256,878 | 3/1981 | Klaus et al. | 542/412 |
| 4,346,161 | 8/1982 | Krutak et al. | 430/223 |
| 5,228,688 | 7/1993 | Davis | 473/290 |
| 5,565,324 | 10/1996 | Still et al. | 435/6 |

FOREIGN PATENT DOCUMENTS

| | | |
|---|---|---|
| 0006154 | 1/1980 | European Pat. Off. . |
| 0207345 | 1/1987 | European Pat. Off. . |
| 0364598 | 4/1990 | European Pat. Off. . |
| 0399814 | 11/1990 | European Pat. Off. . |
| 2513337 | 10/1976 | Germany . |
| 2724445 | 12/1977 | Germany . |
| 4029771 | 3/1992 | Germany . |
| 4119767 | 12/1992 | Germany . |
| 1394366 | 5/1975 | United Kingdom . |
| WO 93/08197 | 4/1993 | WIPO . |
| WO 9408051 | 4/1994 | WIPO . |

OTHER PUBLICATIONS

Combinatorial Synthesis of Small Organic Molecules, F. Balkenhol et al., *Angew. Chem. Int. Ed. Engl.* (1996), 35, 2288–2337.
Certified English Translation of K. Gewald et al. *Chem. Ber.*, pp. 1–10, 1996, vol. 99, 94.
Carabateas, P.M. et al. "Analgesic Antagonists. I. 4–Substituted 1–Acyl–2,3,4,5–tetrahydro–1H–1,4–benzodiazepines" *J. Med. Chem.* 9:6–10 (1966).
DeGrado, W.F. et al. "Polymer–Bound Oxime Esters as Supports for Solid–Phase Peptide Synthesis. Preparation of Protected Peptide Fragments" *J. Org. Chem.* 45:1295–1300 (1980).
DeWitt, S.H. et al "Diversomers: An Approach to Nonpeptide, Nonoligomeric Chemical Diversity" *Proc. Natl. Acad. Sci. USA* 90:6909–6913 (1993).
Errede, L.A. et al. "Acylanthranils.3. The Influence of Ring Substituents on Reactivity and Selectivity in the Reaction of Acylanthranils with Amines" *J. Org. Chem.* 42(1):12–18 (1977).
Foster, C.H. et al. "Novel One–Pot Synthesis of 4–Aminoquinazolines" *J. Org. Chem.* 41(15) :2646–2647 (1976).
Gewald, K. et al. "2–Amino–thiopene aus methylenaktiven Nitrilen, Carbonylverbindungen und Schwefel" *Chem. Ber.* 99:94–100 (1966).
Gordon, E.M. et al. "Applications of Combinatorial Technologies to Drug Discovery. 2. Combinatorial Organic Synthesis, Library Screening Strategies, and Future Directions" *Journal of Medical Chemistry* 37(10):1385–1401 (1994).
Houghten, R.A. et al. "Generation and Use of Synthetic Peptide Cominatorial Libraries for Basis Research and Drug Discovery" *Naturem* 354:84–86 (1991).
Kim, D.H. "Improved Synthesis of 1,4–Benzodiazepine–2, 5–diones" *J. Heterocyclic Chem.*12:1323–1324 (1975).
Mayer, J.P. et al. "Solid Phase Synthesis of 1,4–Benzodiazepine–2,5–diones" *Tetrahedron Letters* 37(45):8081–8084 (1996).
Mitscher, L.A. et al. "Quinolone Antimicrobial Agents. 1. Versatile New Synthesis of 1–Alkyl–1, 4–dihydro–4–oxo–3–quinolinecarboxylic Acids" *Journal of Medical Chemistry* 21(5):485–489 (1978).
Molina, P. et al. "Heterocyclic Synthesis via a Tandem Aza–wittig Reaction/Heterocumulene–mediated Annulation reaction. New Methodology for the Preparation of Quinazoline Derivatives" *Tetrahedron Letters* 29(31):3849–3852 (1988).
Müller, C.E. et al. "Chiral Pyrrolo[2,3–d]pyrimidine and Pyrimido[4,5–b]indole Derivatives: Structure–Activity Relationships of Potent, Highly Stereoselective $A_1$–Adenosine Receptor Antagonists" *J. Med. Chem.* 39:2482–2491 (1996).
Roth, H.J. et al. "Synthese von 2–Amino–3–cyano–pyrrolen" *Arch. Pharmaz.* 308(75):179–185 (1975).
Sampson, N.S. et al. "Attempted de Novo Design, Synthesis, and Evaluation of a Ligand for the Allosteric Site of Phosphofructokinase" *J. Org. Chem.* 56:7179–7183 (1991).
Takashi, M. et al. *Nippon Kaguku Kaishi* 8:1259 (1972).

*Primary Examiner*—Johann Richter
*Assistant Examiner*—Taofiq A. Solola
*Attorney, Agent, or Firm*—Lahive & Cockfield, LLP; Giulio A. DeConti, Jr. Esq.; Peter C. Lauro, Esq.

[57] ABSTRACT

Methods for preparing thiophene and pyrrole-based heterocyclic compounds are disclosed. Also disclosed are libraries of thiophene and pyrrole-based heterocyclic compounds, methods for preparing the libraries of thiophene and pyrrole-based heterocyclic compounds, and methods for using the thiophene and pyrrole-based heterocyclic compounds and compound libraries of the invention. The compounds of the invention have biological activity including anti-cancer activity.

64 Claims, No Drawings

SYNTHESIS AND USE OF THIOPHENE- AND PYRROLE-BASED HETEROAROMATIC COMPOUNDS

BACKGROUND OF THE INVENTION

Recent advances in organic synthesis and screening of compounds have led to the discovery of new classes of agents useful as inhibitors of enzymes, agonists or antagonists of cell surface receptors, and the like. Although peptide-based ligands can have good activity in modulation of biochemical events, the susceptibility of polypeptides to rapid in vivo degradation has prompted researchers to seek non-peptidic active compounds.

Heteroaromatic compounds are ubiquitous in biochemistry, pharmacology, agricultural chemistry, and the like. Synthetic heteroaromatic compounds have been used as analgesics, antibiotics, anti-viral compounds, pesticides, and herbicides, among other uses. Although many methods are known for synthesizing heteroaromatic compounds, some of these methods may not be readily adaptable to the production of a variety of compounds (i.e., compounds bearing a variety of functional groups). Known methods may also not be well-suited to combinatorial syntheses, by which large numbers of compounds can be rapidly synthesized.

One method for synthesis of substituted thiophene compounds that has been reported (Gewald, K, E. Schinke, and H. Bottcher, *Chem Ber.*, 1966 99, 94; Sampson, N. and P. Bartlett, *J. Org Chem*, 1991 56, 7179) involved reaction of a ketone or β-ketoester with a cyanoacetate ester and elemental sulfur. Reported reaction solvents included ethanol, t-butanol, and dimethylformamide. However, reported yields were often only low to moderate. A related method for the synthesis of pyrroles has been reported (Roth, H. and K. Eger, *Arch. Pharm.*, 1975 308. 179; Muller, C., et al., *J. Med Chem.* 1996 39, 2482). Again, however, yields are not uniformly high for all substrates.

Accordingly, improved methods for synthesis of heterocycles are desirable.

SUMMARY OF THE INVENTION

This invention pertains to synthesis of substituted thiophene and pyrrole heterocycles, to compounds and libraries of compounds which can be synthesized according to the methods of the invention, and to methods for using the compounds to promote or inhibit biochemical reactions or pathways.

In another aspect, the invention provides a compound represented by the formula (Formula Ia):

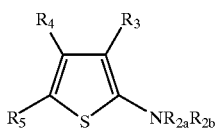

in which
 $R_{2a}$ and $R_{2b}$ are each, independently selected from the group consisting of hydrogen, alkyl, aryl, alkylcarbonyl, arylcarbonyl, alkoxycarbonyl, aryloxycarbonyl, aminocarbonyl, alkylsulfonyl, or arylsulfonyl; or $R_{2a}$ and $R_{2b}$ taken together with the nitrogen atom to which they are attached, form a 3- to 8-membered ring;
 $R_3$ is hydrogen, —CN or —C(O)$R_6$;
 $R_4$ is alkyl (including aralkyl) or aryl;

$R_5$ is hydrogen, halogen, alkyl, aryl, or —C(O)$R_{5'}$; and
 $R_{5'}$ and $R_6$ are each independently selected from the group consisting of hydroxy, alkyl, aryl, alkoxy, aryloxy, —SH, alkylthio, arylthio, amino, or a linker to a solid support;

or a salt thereof.

In preferred embodiments, $R_{2a}$ is hydrogen and $R_{2b}$ is selected from the group consisting of hydrogen, alkyl, aryl, alkylcarbonyl, arylcarbonyl, alkoxycarbonyl, aryloxycarbonyl, aminocarbonyl, alkylsulfonyl, arylsulfonyl or aminosulfonyl; or $R_{2a}$ and $R_{2b}$ taken together with the nitrogen atom to which they are attached, form a 3- to 8-membered ring; $R_3$ is hydrogen or —COR$_6$; $R_4$ is alkyl or aryl; $R_5$ is —C(O)$R_{5'}$; and $R_{5'}$ and $R_6$ are each independently selected from the group consisting of hydroxy, alkyl, aryl, alkoxy, aryloxy, —SH, alkylthio, arylthio, amino, or a linker to a solid support.

In preferred embodiments, $R_{2a}$ is hydrogen and $R_{2b}$ is arylcarbonyl. In certain embodiments, $R_6$ is hydroxy. In other embodiments, $R_6$ is a linker to a solid support. In certain embodiments, $R_4$ is methyl. In certain embodiments, $R_{5'}$ is amino. In particularly preferred embodiments, the compound is represented by the formula (Formula Ib):

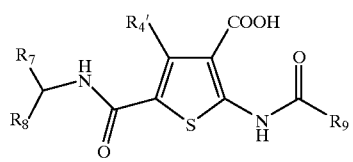

in which
 $R_{4'}$ is alkyl;
 $R_7$ is hydrogen or alkyl;
 $R_8$ is aryl; and
 $R_9$ is alkyl or aryl;
or a salt thereof.

In more preferred embodiments, $R_7$ is cyclopropyl; $R_8$ is substituted or unsubstituted phenyl; and/or $R_9$ is substituted or unsubstituted phenyl.

In another aspect, the invention provides a method for preparing a compound represented by the formula (Formula Ia):

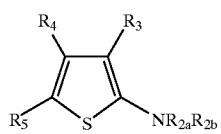

in which
 $R_{2a}$ and $R_{2b}$ are each, independently selected from the group consisting of hydrogen, alkyl, aryl, alkylcarbonyl, arylcarbonyl, alkoxycarbonyl, aryloxycarbonyl, aminocarbonyl, alkylsulfonyl, or arylsulfonyl; or $R_{2a}$ and $R_{2b}$ taken together with the nitrogen atom to which they are attached, form a 3- to 8-membered ring;
 $R_3$ is hydrogen, —CN or —C(O)$R_6$;
 $R_4$ is alkyl (including aralkyl) or aryl;
 $R_5$ is hydrogen, halogen, alkyl, aryl, or —C(O)$R_{5'}$; and $R_{5'}$ and $R_6$ are each independently selected from the group consisting of hydroxy, alkyl, aryl, alkoxy, aryloxy, —SH, alkylthio, arylthio, amino, or a linker to a solid support;

or a salt thereof,

The method includes the step of reacting a compound represented by the formula $R_4C(O)CH_2R_5$ with a compound represented by the formula $CNCH_2CN$ or $R_6C(O)CH_2CN$, and with elemental sulfur, in the presence of a pyridine compound, under conditions such that a compound of Formula Ia is prepared.

In preferred embodiments, $R_3$ is —$C(O)R_6$. In preferred embodiments, at least about 1–2 moles of sulfur are used for each mole of $R_4C(O)CH_2R_5$. In preferred embodiments, the compound represented by the formula $R_6C(O)CH_2CN$ is t-butylcyanoacetate. In preferred embodiments, $R_{2a}$ is hydrogen. In preferred embodiments, at least one of $R_{5'}$ and $R_6$ is a linker to a solid support, and the compound of Formula Ia is prepared by solid-phase synthesis. In preferred embodiments, the method includes the further step of purifying the compound of Formula Ia. In preferred embodiments, the reaction is performed in a solvent comprising pyridine; the solvent can comprise at least about 50% pyridine.

In another aspect, the invention provides a library of compounds of Formula Ia. In a preferred embodiment, the library comprises at least 30 compounds.

In another aspect, the invention provides a method for preparing a library of compounds of Formula Ia. The method includes the step of reacting a first compound represented by the formula $R_4C(O)CH_2R_5$ with a second compound represented by the formula $R_6C(O)CH_2CN$ and with elemental sulfur in the presence of a pyridine compound; in which at least one of the first and second compounds is provided as a variegated population, under conditions such that a library of compounds of Formula Ia is prepared.

In another aspect, the invention provides a method for inhibiting unwanted cell growth in a subject. The method includes the step of administering to the subject an effective amount of a compound of Formula Ia, such that unwanted cell growth is inhibited in the subject. In preferred embodiments, the unwanted cell growth is due to cancer. In a preferred embodiment, the administering step includes administering a compound of Formula Ib.

In another aspect, the invention provides a compound of Formula Ia in a pharmaceutically-acceptable carrier.

In another aspect, the invention provides a compound represented by the formula (Formula II):

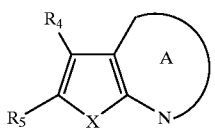

in which

X is S or $NR_1$;

$R_1$ is hydrogen, alkyl or aryl;

$R_4$ is alkyl or aryl;

$R_5$ is hydrogen, halogen, alkyl, aryl, or —$C(O)R_{5'}$;

$R_{5'}$ is selected from the group consisting of hydroxy, alkyl, aryl, alkoxy, aryloxy, —SH, alkylthio, arylthio, amino, or a linker to a solid support; and A represents a ring structure having from 5 to 7 atoms in the ring structure, and having one or two heteroatoms in the ring;

or a salt thereof.

In certain embodiments, $R_{5'}$ is an amino acyl moiety.

DETAILED DESCRIPTION OF THE INVENTION

The present invention relates to thiophene and pyrrole-based heteroaromatic compounds, to methods of making such compounds, to libraries of the compounds, and to methods of using the compounds and libraries.

Definitions

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "aryl" as used herein includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The terms "heterocyclyl" or "heterocyclic group" refer to 3- to 10-membered ring structures, more preferably 4- to 7-membered rings, which ring structures include one to four heteroatoms. Heterocyclyl groups include pyrrolidine, oxolane, thiolane, oxazole, piperidine, piperazine, morpholine, lactones, lactams such as azetidinones and pyrrolidinones, lactones, cyclic anhydrides, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, aralkyl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "amino" as used herein, refers to a moiety represented by the formula —$NR_aR_b$, in which $R_a$ and $R_b$ are each independently hydrogen, alkyl, aryl, or heterocyclyl, or $R_a$ and $R_b$ together with the nitrogen atom to which they are attached, form a 3- to 8-membered heterocyclic ring.

The term "linker group," as used herein, refers to a linking or spacing moiety which can be used to covalently or non-covalently link a compound to a solid support. Linker groups suitable for use in the invention are known in the art for use in solid-phase synthesis. It will be appreciated by the skilled artisan that a linker group can be a direct bond to a solid support, such a resin bead.

The term "pyridine compound," as used herein, refers to pyridine and substituted pyridines, including lutidine, 2,6-di-t-butylpyridine, and the like. However, a pyridine compound, as used herein, can also be a fused compound such as quinoline, and substituted derivatives thereof. In general, a pyridine compound suitable for use in the present invention will be have appreciable basicity, e.g., a basicity similar to pyridine.

The term "leaving group", as used herein, refers to a functionality that upon heterolytic bond cleavage departs with an electron pair.

The term "amino acyl" as used herein, refers to a residue of an amino acid. An "amino acid" as used herein, refers to natural and synthetic amino acids, including analogs, derivatives, and mimetics thereof. An amino acyl moiety can also include a peptide chain, preferably having from two to five amino acid residues in the peptide chain, more preferably having three or four amino acids in the peptide chain.

The term "substantially pure," as used herein, refers to a compound which is substantially free of impurities, including (but not limited to) starting materials, side products, and the like. A compound is "substantially pure" if it comprises at least about 80%, more preferably 90%, still more preferably at least about 95% of the composition. If a single isomer of a compound is desired (e.g., a single diastereomer, enantiomer, or regioisomer), the compound is preferably substantially free of any undesired isomers (e.g., the unwanted enantiomer, diastereomers, or regioisomers), i.e., the desired isomer comprises at least about 80%, more preferably 90%, still more preferably at least about 95% of the weight of the isomers present in the composition.

The term "solid support," as used herein, refers to a solid or insoluble phase which can serve as a support or "scaffold" for the preparation of functionalized compounds by solid-phase chemistry. Many solid supports are known in the art and some are commercially available. Exemplary solid supports include cross-linked divinylbenzene-styrene (polystyrene), controlled pore glass (CPG), polyacrylamides, poly(ethyleneglycol)monomethyl ether and poly(ethylene glycol) (PEG), silica gel, cellulose, acrylic acid grafted polypropylene, and the like. Commercially-available solid supports include Wang resin, Merrifield resin, Tentagel, Rapp resin, and the like.

The term "subject," as used herein, refers to an animal, more preferably a warm-blooded animal, most preferably a mammal, including cattle, sheep, pigs, horses, dogs, cats, rats, mice, and (most preferably) humans.

It will be noted that the structure of some of the compounds of this invention can include asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, alkenes can include either the E- or Z-geometry, where appropriate.

I. Compounds

In one aspect, the invention provides substituted thiophene and pyrrole compounds. The compounds of the invention are useful e.g., as enzyme inhibitors (e.g., of phosphofructokinase), as agonists or antagonists of cell surface receptors (e.g., as $A_1$-adenosine receptor antagonists or agonists or antagonists of G-protein coupled receptors), and the like. The compounds of the invention are also useful as ligands for neuropeptide receptors such as GRP, NMB, cholecystokinin (CCK) and neurokinin (NK), or as ligands for the FcεRI receptor. In addition, as described herein, the inventors have now discovered that certain thiophne-based heteroaromatic compounds of the invention exhibit anti-cancer activity. Accordingly, the compounds of the invention are useful as therapeutic agents, e.g., for the treatment of cancer. It will also be appreciated that compounds of the invention are useful as synthetic intermediates for the production of a variety of highly functionalized heteroaromatic compounds, including thiophenes, pyrroles, and fused compounds such as fused analogs of quinazolones (see, e.g., Example 1, infra). Thus, the invention provides a variety of substituted heteroaromatic compounds useful for synthesis of pharmaceuticals and the like.

In one embodiment, the invention provides compounds represented by the formula (Formula I):

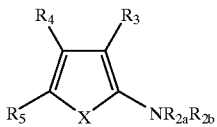

in which

X is S or $NR_1$;

$R_1$ is hydrogen, alkyl (including aralkyl) or aryl;

$R_{2a}$ and $R_{2b}$ are each, independently selected from the group consisting of hydrogen, alkyl, aryl, alkylcarbonyl, arylcarbonyl, alkoxycarbonyl, aryloxycarbonyl, aminocarbonyl, alkylsulfonyl, arylsulfonyl or aminosulfonyl (preferably dialkylaminosulfonyl); or $R_{2a}$ and $R_{2b}$ taken together with the nitrogen atom to which they are attached, form a 3 to 8-membered ring;

$R_3$ is hydrogen, —CN or —C(O)$R_6$;

$R_4$ is alkyl (including aralkyl) or aryl;

$R_5$ is hydrogen, halogen, alkyl, aryl, or —C(O)$R_{5'}$; and $R_{5'}$ and $R_6$ are each independently selected from the group consisting of hydroxy, alkyl, aryl, alkoxy, aryloxy, —SH, alkylthio, arylthio, amino (including amino acyl), or a linker to a solid support;

or a salt thereof.

In one embodiment, X is S, i.e., the compound of Formula I is a thiophene and can be represented by the formula (Formula Ia):

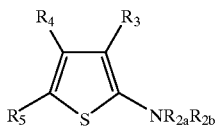

in which $R_{2a}$, $R_{2b}$, $R_3$, $R_4$, and $R_5$ are as described above. In one embodiment, both $R_{2a}$ and $R_{2b}$ are hydrogen. In a preferred embodiment, $R_{2a}$ and $R_{2b}$ taken together with the nitrogen atom to which they are attached, form a 3- to 8-membered ring, preferably a pyrrole ring. In a particularly preferred embodiment, $R_{2a}$ is hydrogen and $R_{2b}$ is alkylcarbonyl or arylcarbonyl, more preferably benzoyl or 3-phenylpropanoyl. In a preferred embodiment, $R_3$ is —C(O)$R_6$. In a more preferred embodiment, $R_6$ is hydroxy, i.e., $R_3$ is —COOH. In a preferred embodiment, $R_5$ is —C(O)$R_{5'}$. In a particularly preferred embodiment, $R_{5'}$ is an amino group, more preferably an aryl-substituted monoalkylamino group, still more preferably a substituted or unsubstituted benzylamino group, including a (3-(trifluoromethyl)phenyl)methylamino group or a 1-((4-methoxy)phenyl)-1-cyclopropylmethyl group.

In a preferred embodiment, $R_4$ is alkyl, more preferably methyl. In certain preferred embodiments, at least one of $R_6$ and $R_5$, is a linker to a solid support. In certain preferred embodiments, at least one of $R_6$ and $R_{5'}$ is amino acyl, e.g., the compound of Formula I comprises at least one amino acid residue.

In a particularly preferred embodiment, the compound of Formula Ia can be represented by the formula (Formula Ib):

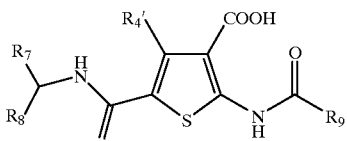

in which $R_{4'}$ is alkyl;

$R_7$ is hydrogen or alkyl;

$R_8$ is aryl; and $R_9$ is alkyl or aryl.

In preferred embodiments, $R_{4'}$ is methyl. In preferred embodiments, $R_7$ is cycloalkyl, more preferably cyclopropyl. In certain preferred embodiments, $R_7$ is hydrogen. In preferred embodiments, $R_8$ is substituted or unsubstituted phenyl, more preferably 3-trifluoromethylphenyl or 4-methoxyphenyl. In preferred embodiments, $R_9$ is substituted or unsubstituted phenyl or 2-phenylethyl.

In another embodiment, X is $NR_1$, i.e., the compound of Formula I is a pyrrole and can be represented by the formula (Formula Ic):

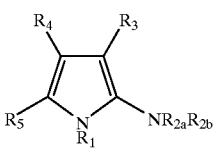

in which $R_1$, $R_{2a}$, $R_{2b}$, $R_3$, $R_4$, and $R_5$ are as described above. In a preferred embodiment, $R_1$ is alkyl (including aralkyl) or aryl. In a more preferred embodiment, $R_1$ is methyl. In a preferred embodiment, both $R_{2a}$ and $R_{2b}$ are hydrogen. In another embodiment, $R_{2a}$ and $R_{2b}$ taken together with the nitrogen atom to which they are attached, form a 3- to 8-membered heterocyclic ring, preferably a pyrrole ring. In a preferred embodiment, $R_5$ is —C(O)$R_{5'}$. In certain preferred embodiments, at least one of $R_6$ and $R_5$ is a linker to a solid support. In certain preferred embodiments, $R_4$ and $R_5$ are the same, and are preferably alkyl (more preferably methyl), phenyl or heteroaromatic (such as pyridinyl). In a preferred embodiment, $R_3$ is —C(O)$R_6$. In a more preferred embodiment, $R_6$ is hydroxy, i.e., $R_3$ is —COOH.

In another embodiment, the invention provides a compound represented by the formula (Formula II):

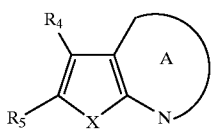

in which X, R₄ and R₅ are as defined above, and A represents a ring structure having from 5 to 7 atoms in the ring structure, and having one or two heteroatoms in the ring. The A ring can include from one to three unsaturations (e.g., double bonds) and can be unsubstituted or substituted, e.g., with one or more moieties which can substitute an alkyl or aryl group as described supra. Thus, in exemplary embodiments, a compound of Formula II can have any of the following structures (Formulas IIa–IIg):

IIa
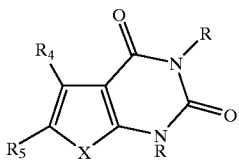

IIb
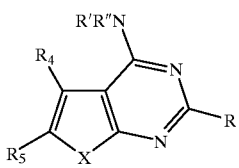

IIc
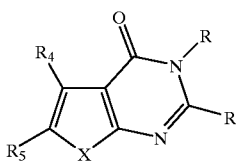

IId
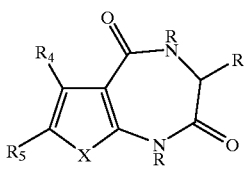

IIe
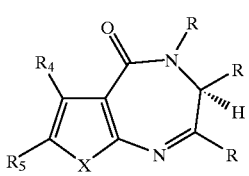

IIf
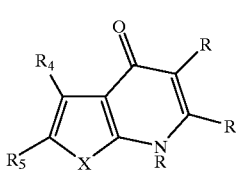

IIg
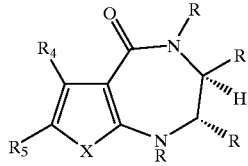

in which R, R', and R" are hydrogen, alkyl, aryl, and the like.

In preferred embodiments of compounds of Formula II, X is S.

Compounds of Formula II are useful, e.g., as described herein for compounds of Formula I, e.g., as anti-cancer agents, as inhibitors of enzymes and receptors, and the like; and as pharmaceutical agents such as anti-depressants, anxiolytics, and anti-viral agents.

II. Methods For Preparing Heterocyclic Compounds

In another aspect, the invention provides methods for preparing heterocyclic compounds, including substituted pyrroles and thiophenes. The methods of the invention can provide an efficient synthetic route to a variety of substituted heteroaromatic compounds useful, e.g., as described supra, and for synthesis of pharmaceuticals and the like.

In one embodiment, the invention provides a method for preparing a compound represented by the formula (Formula I):

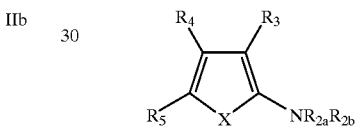

in which

X is S or NR₁;

R₁ is hydrogen, alkyl (including aralkyl) or aryl;

R$_{2a}$ and R$_{2b}$ are each, independently selected from the group consisting of hydrogen, alkyl, aryl, alkylcarbonyl, arylcarbonyl, alkoxycarbonyl, aryloxycarbonyl, aminocarbonyl, alkylsulfonyl, arylsulfonyl or aminosulfonyl (preferably dialkylaminosulfonyl); or R$_{2a}$ and R$_{2b}$ taken together with the nitrogen atom to which they are attached, form a 3 to 8-membered ring;

R₃ is hydrogen, —CN or —C(O)R₆;

R₄ is alkyl (including aralkyl) or aryl;

R₅ is hydrogen, halogen, alkyl, aryl, or —C(O)R₅·; and

R₅· and R₆ are each independently selected from the group consisting of hydroxy, alkyl, aryl, alkoxy, aryloxy, —SH, alkylthio, arylthio, amino (including amino acyl), or a linker to a solid support;

or a salt thereof.

In one embodiment, X is S, i.e., the compound of Formula I is a thiophene and can be represented by the formula (Formula Ia):

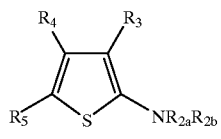

in which R$_{2a}$, R$_{2b}$, R₃, R₄, and R₅ are as described above. The method includes the step of reacting a compound represented by the formula $R_4C(O)CH_2R_5$ with a compound represented by the formula $CNCH_2CN$ or $R_6C(O)CH_2CN$ in the presence of elemental sulfur and a pyridine compound, such that a compound of Formula I is prepared. In a preferred embodiment, $R_3$ is $—C(O)R_6$. In preferred embodiments, at least about 1–2 moles of sulfur are used for each mole of $R_4C(O)CH_2CR_5$. In a preferred embodiment, the compound represented by the formula $R_6C(O)CH_2CN$ is t-butylcyanoacetate. In a preferred embodiment, both $R_{2a}$ and $R_{2b}$ are hydrogen. In another embodiment, $R_{2a}$ and $R_{2b}$ taken together with the nitrogen atom to which they are attached, form a 3- to 8-membered ring, preferably a pyrrole ring. In a preferred embodiment, $R_5$ is $—C(O)R_{5'}$. In preferred embodiments, an amine base, such as triethylamine or diethylamine, is present during the reacting step. In certain preferred embodiments, at least one of $R_6$ and $R_{5'}$ is a linker to a solid support, and the compound of Formula I is prepared by solid-phase synthesis (especially for preparation of libraries of compounds; see infra). In certain embodiments, the method includes the further step of purifying the products (e.g., by crystallization, distillation, chromatography, and the like; or, in the case of reactions performed on a solid support, by washing). In certain preferred embodiments, at least one of $R_6$ and $R_{5'}$ is amino acyl, e.g., the compound of Formula I comprises at least one amino acid residue. In a preferred embodiment, the compound of Formula I is prepared in at least about 50% yield, more preferably at least about 70% yield, more preferably at least about 80% yield, and most preferably at least about 90% yield. In certain embodiments, the method includes further functionalization steps, including esterification, amidation, reduction, oxidation, substitution, and the like. In a preferred embodiment, the compound of Formula Ia is prepared in substantially pure form.

In another embodiment, X is $NR_1$, i.e., the compound of Formula I is a pyrrole and can be represented by the formula (Formula Ic):

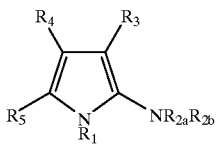

in which $R_1$, $R_{2a}$, $R_{2b}$, $R_3$, $R_4$, and $R_5$ are as described above. The method includes the step of reacting a compound represented by the formula $R_4CH(Y)C(O)R_5$, in which Y is —OH or a good leaving group (e.g., a halogen such as chlorine, bromine, or iodine), with a compound represented by the formula $R_6C(O)CH_2CN$ or $CH_2(CN)_2$ and a compound represented by the formula $NH_2R_1$, in the presence of a pyridine compound, such that a compound of Formula I is prepared. In a preferred embodiment, the reacting step includes the step of reacting the compound represented by the formula $R_4CH(Y)C(O)R_5$ with the amine compound represented by the formula $NH_2R_1$, in the presence of an acid catalyst (such as e.g., HCl or toluenesulfonic acid), preferably in a solvent, to form an α-aminoketone product, and then reacting the α-aminoketone product with the compound represented by the formula $R_6C(O)CH_2CN$ or $CH_2(CN)_2$, in the presence of a pyridine compound (and preferably in the presence of a strong base such as KOH or NaOH, and preferably in a solvent such as ethylene glycol at elevated temperature), such that a compound of Formula I is prepared. In a preferred embodiment, $R_1$ is alkyl (including aralkyl) or aryl. In a preferred embodiment, $R_1$ is methyl. In a preferred embodiment, both $R_{2a}$ and $R_{2b}$ are hydrogen. In another embodiment, $R_{2a}$ and $R_{2b}$ taken together with the nitrogen atom to which they are attached, form a 3- to 8-membered heterocyclic ring, preferably a pyrrole ring. In a preferred embodiment, $R_5$ is $—C(O)R_{5'}$. In certain preferred embodiments, at least one of $R_6$ and $R_{5'}$ is a linker to a solid support, and the compound of Formula I is prepared by solid-phase synthesis. In certain embodiments, the method includes the further step of purifying the products (e.g., by crystallization, distillation, chromatography, and the like; or, in the case of reactions performed on a solid support, by washing). In a preferred embodiment, the compound of Formula I is prepared in at least about 50% yield, more preferably at least about 70% yield, more preferably at least about 80% yield, and most preferably at least about 90% yield. In certain embodiments, the method includes further functionalization steps, including esterification, amidation, reduction, oxidation, substitution, and the like. In a preferred embodiment, the compound of Formula Ic is prepared in substantially pure form. In certain preferred embodiment, $R_4$ and $R_5$ are the same, and are preferably alkyl (more preferably methyl), phenyl or heteroaromatic (such as pyridinyl). In a preferred embodiment, $R_3$ is $—C(O)R_6$. In a more preferred embodiment, $R_6$ is hydroxy, i.e., $R_3$ is —COOH.

It has now been discovered that improved yields of heteroaromatic compounds (e.g., of Formula I) can be obtained by use of pyridine as a reaction solvent. Accordingly, in preferred embodiments of the methods described herein (preferably in which X is S), the pyridine compound is pyridine. In a preferred embodiment, the pyridine compound is employed as a solvent, e.g., the reaction is performed in a solvent comprising at least about 10% pyridine, more preferably at least about 30% pyridine, more preferably at least about 50% pyridine, and still more preferably at least about 80% pyridine (v/v). In a most preferred embodiment, the solvent is more than about at least 90% pyridine, or the solvent is substantially pure pyridine.

The present invention can conveniently be performed in the solid phase, and can also be performed though use of automated or semi-automated techniques, including use of robotic workstations. Commercially available computer controlled robots can reduce the amount of the intensive manual labor involved in small molecule library synthesis, and thereby increase throughput in compound synthesis.

The solid phase synthesis of tetrasubstituted thiophenes can parallel the solution phase synthesis. For example, a cyanoacetate compound can be linked to an alcohol containing resin (e.g., Wang, oxime (see, e.g., DeGrado, W. F.; Kaiser, E. T. *J. Org Chem.* (1980) 45:1295–1300) or tetrafluorophenol (TFP) (see, e.g., co-pending commonly assigned U.S. application Ser. No. 08/835,623 entitled "Supports For Solid Phase Synthesis")) by standard esterification techniques. The thiophene template can then be formed by reaction with β-ketoesters, utilizing the improved conditions described herein (see, e.g., Scheme 5). The thiophene can be further functionalized, e.g., as described herein for the solution phase synthesis, to ultimately yield either 3-thiophene carboxylic acids (Wang resin) or the corresponding amides (e.g., by transamidation and concomitant cleavage from oxime or TFP resin) by standard solid phase protocols. The solid phase synthesis of thiophenes allows for the production of pure compounds in a rapid manner. An illustrative solid-phase synthesis is described in Example 16, infra.

The reactions of the present invention may be performed under a wide range of conditions, though it will be understood that conditions recited herein are not limitative and only correspond to a preferred mode of the process of the invention.

In general, it is desirable that reactions are run using mild conditions that will not adversely affect the reactants, the intermediates, or the desired product. For example, the reaction temperature influences the speed of the reaction. The reactions will usually be run at temperatures in the range of −78° C. to 100° C., more preferably in the range −20° C. to 50° C. and still more preferably in the range −20° C. to 25° C.

In general, reactions according to the invention will be performed in the liquid phase, e.g., in solution or suspension. When solvents other than pyridine are used (e.g., as co-solvents with pyridine), such solvents preferably do not react with the reactants or products of the inventive methods. Typical solvents include, e.g., alcohols such as methanol, ethanol, isopropanol, and t-butanol; ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. In preferred embodiments, the reactions are conducted under anhydrous conditions. In certain embodiments it is preferable to perform the reactions under an inert atmosphere of a gas such as nitrogen or argon.

Compounds of Formula II can be prepared, e.g., from compounds of Formula I, by the methods described herein (see, e.g., Example 1) or by methods well known to the ordinarily skilled artisan. Thus, for example, methods known for the synthesis of fused aromatic compounds from anthranilic acids are well known (see, e.g., references 6–16). Accordingly, similar transformations of the thiophene and pyrrole templates of the invention (i.e., of Formula I) can be employed to prepare a variety of fused compounds, e.g., of Formula II.

III. Libraries and Library Synthesis

In another aspect, the invention provides libraries of heteroaromatic compounds of Formula I (including Ia–Ic) or Formula II. Libraries of the invention are useful, e.g., for drug discovery. For example, a library of the invention can be screened (e.g., according to the methods described herein) to determine whether the library includes compounds having a pre-selected activity. Thus, for example, a library can be screened to determine whether compounds of the library have enzyme inhibitory activity or any other activity which can be detected in vitro or in vivo, e.g., anti-inflammatory activity, cell growth stimulatory activity, anti-neoplastic activity, and the like. Such screening assays are useful e.g., for identification of active compounds and for determination of structure-activity relationships for the design of improved pharmaceutical agents.

The synthesis of combinatorial libraries is well known in the art and has been reviewed (see, e.g., E. M. Gordon et al., *J. Med Chem.* 37:1385–1401 (1994)). Thus, the subject invention contemplates methods for synthesis of combinatorial libraries of compounds of Formula I. Such libraries can be synthesized according to a variety of methods. For example, a "split-pool" strategy can be implemented in the following way: beads of a functionalized polymeric support, to which cyanoacetic acid has been covalently linked (see, e.g., Example 16, infra), are placed in a plurality of reaction vessels. To each aliquot of beads is added a solution of a different β-ketoester (e.g., $R_4C(O)CH_2C(O)R_5$), and the reactions proceed to yield a plurality of immobilized substituted thiophene compounds. The aliquots of derivatized beads are then washed, "pooled" (i.e., recombined), and the pool of beads is again divided, with each aliquot being placed in a separate reaction vessel. To each reaction vessel is added a solution of a different acid halide (e.g., acid chloride, chlorocarbonate, or sulfonyl chloride) in solution, and reaction occurs to yield a plurality of reaction vessels each containing a plurality of compounds of Formula I ($R_2$=alkylcarbonyl, arylcarbonyl, alkoxycarbonyl, aryloxycarbonyl, alkylsulfonyl, or arylsulfonyl) immobilized on solid support. The library of immobilized compounds can then be washed to remove impurities. In certain embodiments, the compound of Formula I can be further treated (e.g., by cleavage from the solid support, if desired, and further reaction (e.g., substitution or further functionalization)), e.g., to yield fused thiophene-quinazolones.

In another illustrative method of combinatorial synthesis, a "diversomer library" is created by a modification of the method of Hobbs DeWitt et al. (*Proc. Natl. Acad. Sci. U.S.A.* 90:6909 (1993)). Aliquots of cyanoacetate-functionalized polymeric support beads are placed in an array of reaction vessels as above, and one of a plurality of different β-ketoesters is introduced into each vessel. After reaction, the beads are washed to yield to yield an array of functionalized thiophenes. Each vessel in the array is then reacted with one of a plurality of primary or secondary amines, thereby cleaving the thiophene compounds from the support and creating a library of soluble thiophene compounds having different amino groups (i.e., $R_5=NR_{3a}R_{3b}$).

Other synthesis methods, including the "tea-bag" technique of Houghten (see, e.g., Houghten et al., *Nature* 354:84–86 (1991)) can also be used to synthesize libraries of compounds according to the subject invention. Furthermore, libraries of compounds can be provided without the use of solid supports, e.g., by parallel solution-phase synthesis in a plurality of reaction vessels. In this embodiment, the use of an automated robotic workstation can increase the ease and speed of the library synthesis (see, e.g., Example 17).

Combinatorial libraries can be screened to determine whether any members of the library have a desired activity, and, if so, to identify the active species. Methods of screening combinatorial libraries have been described (see, e.g., Gordon et al., *J. Med. Chem., op. cit.*). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, calorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assay formats useful for screening the libraries of the invention are known in the art (see, e.g., E. M. Gordon et al., *J. Med. Chem.* 37:1385–1401 (1994)). In certain embodiments, compounds can be screened for activity against chemokine receptors (such $C_{5a}$, I1–8, CCR1–CCR5, TNFα) (see, e.g., International Publication No. WO96/18393), G-protein coupled receptors (such as $A_1$ -adenosine receptors, neuropeptide receptors, and the like), or the FcεRI receptor. Compounds can also be screened as described in Example 17, infra.

Combinatorial libraries of compounds can also be synthesized with "tags" to encode the identity of each member of the library (see, e.g., W. C. Still et al., U.S. Pat. No. 5,565,324 and PCT Publication No. WO 94/08051). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels.

In preferred embodiments, the libraries of compounds of the invention contain at least 2 compounds, more preferably at least about 30 compounds, more preferably at least about 100 compounds, more preferably at least about 500 compounds, and still more preferably at least about 1000 compounds. In certain embodiments, the libraries of the invention can include at lest $10^4$ compounds, $10^5$ compounds, $10^6$ compounds, or $10^7$ compounds. However, in certain preferred embodiments, the libraries of compounds of the invention contain fewer than $10^9$ compounds, more preferably fewer than $10^8$ compounds, and still more preferably fewer than $10^7$ compounds.

A library of compounds is preferably substantially pure, i.e., substantially free of compounds other than the intended products, e.g., members of the library. In preferred embodiments, the purity of a library produced according to the methods of the invention is at least about 50%, more preferably at least about 70%, still more preferably at least about 90%, and most preferably at least about 95%.

The libraries of the invention can be prepared according to the methods of the invention, wherein at least the compound represented by the formula $R_4C(O)CH_2C(O)R_5$ is provided as a variegated population. In a preferred embodiment, the methods for preparing libraries are performed on a solid support (i.e., at least one of the compound represented by the formula $R_4C(O)CH_2C(O)R_5$ or the cyanoacetate is immobilized on a solid support). The term "variegated population", as used herein, refers to a population including at least two different chemical entities, e.g., of different chemical structure. For example, a "variegated population" of β-ketoesters would comprise at least two different β-ketoesters. Similarly, a variegated population of amines comprises at least two different amines.

IV. Pharmaceutical Compositions

In another aspect, the present invention provides pharmaceutically acceptable compositions which comprise a therapeutically-effective amount of one or more of the compounds described above (e.g., Compounds of Formula I or Formula II), formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect, e.g., treating (i.e., preventing or ameliorating) cancer in a subject, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds can contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19)

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound of the invention in the proper medium. Absorption enhancers can also be used to increase the flux of the the compound of the inventionacross the skin. The rate of such flux can be controlled by either providing a rate controlling membrane or dispersing the the compound of the invention in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral or topical administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the derivative (e.g., ester, salt or amide) thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, doses of the compounds of this invention for a patient, when used for the indicated effects, will range from about 0.0001 to about 100 mg per kilogram of body weight per day, more preferably from about 0.01 to about 50 mg per kg per day, and still more preferably from about 0.1 to about 40 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

V. Methods for Treating Proliferative Disorders

In another aspect, the invention provides a method for treating proliferative disorders such as cancer.

In one embodiment, the invention provides a method for inhibiting unwanted cell growth in a subject. The method includes administering to the subject an effective amount of a compound of Formula I, optionally in a pharmaceutically acceptable carrier, such that unwanted cell growth is inhibited. In one embodiment, the unwanted cell growth is due to cancer.

As described in Example 19, infra, compounds of the invention have significant anti-cancer activity in an in vitro screening assay. Accordingly, such compounds can be employed as anti-cancer or anti-proliferative agents to treat a subject suffering from cancer or other proliferative disorders. In another embodiment, the compounds of the invention can be employed to inhibit (e.g., prevent or reduce) cell growth in vitro, e.g., in a cell culture. Particularly preferred compounds for treatment of proliferative disorders include compounds of Formula Ia in which $R_{2a}$ is hydrogen and $R_{2b}$ is arylcarbonyl or aryl-substituted-alkylcarbonyl, $R_3$ is —COOH, $R_4$ is alkyl (more preferably methyl), and $R_5$ is —C(O)$R_{5'}$, in which $R_{5'}$ is aryl-substituted-alkylamino. In a particularly preferred embodiment, $R_{5'}$ is 3-trifluoromethylbenzylamino ((3-trifluoromethylphenyl)methylamino).

In a preferred embodiment, the cancer is a lung cancer, preferably small cell lung carcinoma.

In another embodiment, the invention provides a method for inhibiting cell proliferation. The method includes the step of contacting a cell with an effective amount of a compound of Formula Ia, optionally in a pharmaceutically acceptable carrier, such that cell proliferation is inhibited.

In another embodiment, the invention provides a method for inhibiting ligand binding to a receptor. The method includes the step of contacting a receptor with an effective amount of a compound of Formula I, such that ligand binding to the receptor is inhibited. The compounds of the invention (i.e., compounds of Formula I) can be used, e.g., as enzyme inhibitors (e.g., of phosphofructokinase), as agonists or antagonists of cell surface receptors (e.g., $A_1$-adenosine receptor antagonists or agonists or antagonists of G-protein coupled receptors), and the like. The compounds of the invention are also useful as ligands for neuropeptide receptors such as gastrin-releasing peptide (GRP), neuromedine B (NMB), cholecystokinin (CCK) and neurokinin (NK).

Compounds of the invention useful in the methods of the invention can be determined by one of ordinary skill in the art, in light of the teachings herein, using no more than routine experimentation. Thus, for example, compounds are useful for killing of cancer cells (such as e.g., small cell lung carcinoma) or inducing programmed cell death (apoptosis). Inhibitition of unwanted cell growth, or cancer-cell killing activity, can be tested in in vitro screening assays (e.g., as described in Example 19, infra) to determine anti-cancer activity. Moreover, libraries of compounds can be screened through the use of high-throughput assays (e.g., as described herein) to determine which compounds in a library have a desired activity. For example, compounds of Formula I can be screened for ability to modulate G-protein coupled receptors by use of screening assays designed to detect modulation of such receptors; such assays are well known in the art.

Exemplification

Materials and Methods

In the examples described herein, all temperatures are given in degrees Centigrade (° C.). Mass spectral analysis were performed by M-Scan Inc., West Chester, Pa. using fast atom bombardment, unless otherwise indicated. $^1$H-NMR spectra were recorded at 200 MHz using a Varian Unity 200 spectrometer. Multiplicities indicated are: s=singlet, brs broad singlet, d=doublet, t=triplet, q=quartet, m=multiplet.

Abbreviations: DCM, dichloromethane; EDC: 1-(3-dimethylaminopropyl)-ethylcarbodiimide; EtOAc, ethyl acetate; BOP: benzotriazol-1-yl-oxy-tris(dimethylamino) phosphonium hexafluorophosphate; HOBt: 1-hydroxybenzotriazole.

Flash chromatography (hereinafter "chromatography") was performed on Merck Silica gel 60 (230–400 mesh).

EXAMPLE 1

Solution-Phase Synthesis of Substituted Thiophenes

Scheme 1

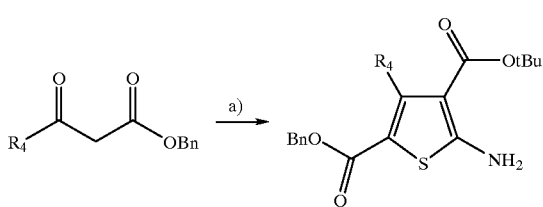

A general scheme for the preparation of tetrasubstituted thiophenes is shown in Scheme 1. Modification of the known procedure (1, 2) led to the production of the thiophene compounds, usually in >70% isolated yield. The use of pyridine as a solvent, t-butyl cyanoactetate and 1–2 equivalents of sulfur (depending on isoform composition) was found to provide optimal yields. In this illustrative synthesis, the substituents at the 2, 3 and 5 positions of the thiophene were suitably chosen for selective functionization and optimum diversification of the library. Functionalization of the thiophene substitutents can be accomplished, e.g., through standard amine acylation and ester manipulation procedures which are well known in the art (3).

Scheme 2 depicts exemplary selective manipulations of the thiophene framework. Amine acylation can occur before or after ester manipulation. The combination of t-butyl and benzyl esters allows for selective manipulation and functionalization, e.g., in library synthesis. Deprotection of the benzyl ester occurred with standard hydrogenation or hydrolysis conditions, and can be achieved without affecting the t-butyl ester. Similarly, selective deprotection of the t-butyl ester occurred upon treatment with trifluoroacetic acid (TFA). The anthranilic acid derivative (5) is a very useful intermediate which has synthetic utility, e.g., as described herein. The two illustrated reaction sequences arrive at the same carboxylic acid compounds (6 and 7). These carboxylic acids can be utilized as handles for diversification at positions C-3 and C-5 through amide bond formation.

Scheme 2

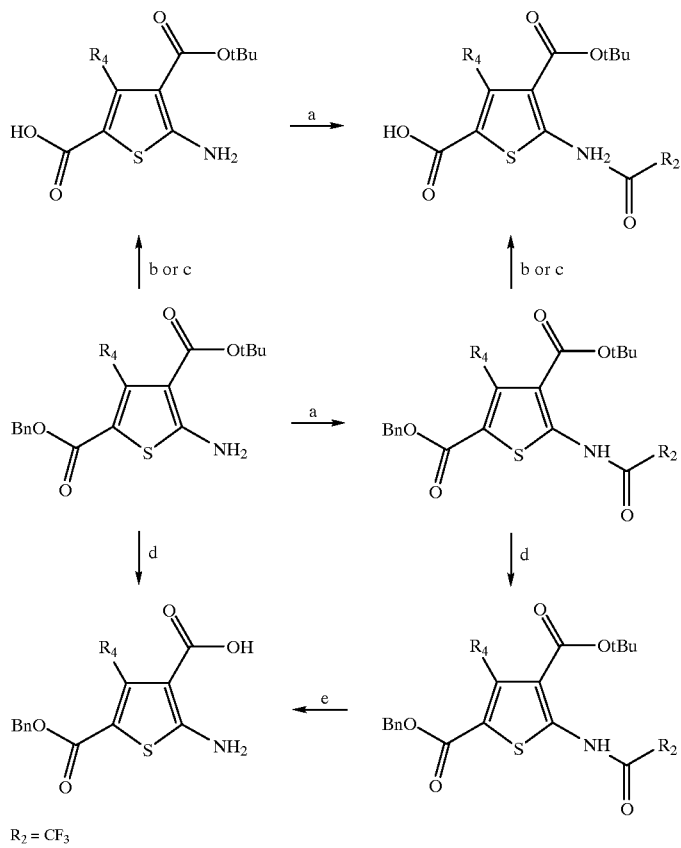

$R_2 = CF_3$ a) ²RCOCl, pyr., DCM b) Pd(OH)₂, H₂, EtOH c) 1.5 M K₂CO₃ (aq). EtOH, reflux or 3M KOH (aq), EtOH d) TFA, DCM e) 10% Na₂CO₃ (aq), EtOH, THF Schemes 3 and 4 show automated and semiautomated reactions utilizing a thiophene "template" of the invention. Carboxylic acid 6 reacted with N-hydroxysuccinimide and EDC to yield the reactive succinate ester 8. In an automated procedure, the succinate esters were combined with the appropriate amine. In general, primary amines reacted at room temperature over 12 hours whereas hindered primary or secondary amines required heating at 70° C. for 6 hours. When the reaction was complete, the robot proceeded to purify the reaction product by use of a work up procedure. The solution was then concentrated and yielded the desired amide (9) in >90% yield and purity. Subsequently, the t-butyl ester was deprotected under acidic conditions (TFA) to give the corresponding 3-carboxylic acid.

Scheme 3

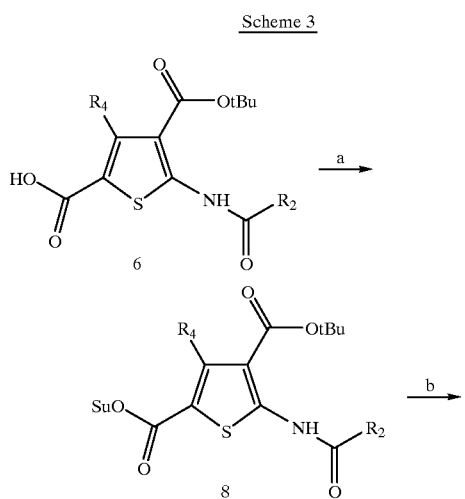

-continued

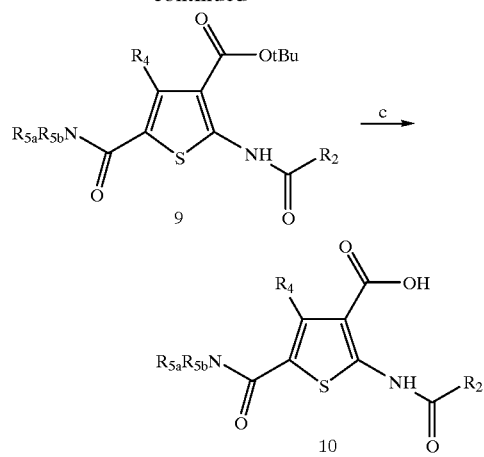

a) EDC, HOBt, HOSu, DMAP
b) HN$^{5a}$•N$^{5b}$, DMF
c) TFA, DCM;
Su = succinimide Functionalization of the 3-carboxylic acid can be accomplished in a similar manner. Carboxylic acid 7 reacted with EDC to give a thiophene-based benzoxazinone analog as the reactive ester. The benzoxazinone analog (which can be isolated if desired) undergoes ring opening with various amines at elevated temperature following literature precedent.(4) In an automated procedure, the benzoxazinone analog was added to various amines and the reaction was heated. Depending on the R₂ substituent, the reaction yielded either the bis-amide (12, R₂=aryl including heteroaryl) or an amidine intermediate which can undergo cyclodehydration to the quinazolones (13), which can be further converted to the amino-substituted thiophene quinazoline analogs (15) as shown.

Scheme 4

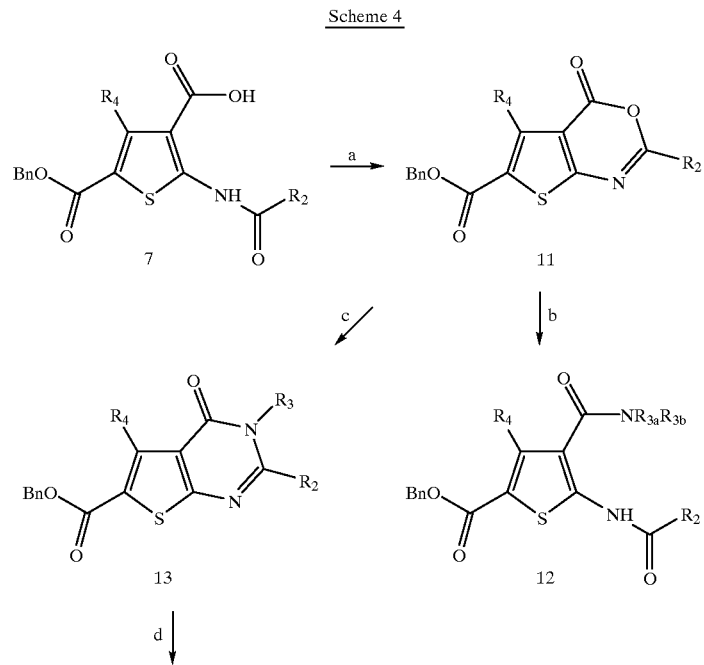

-continued

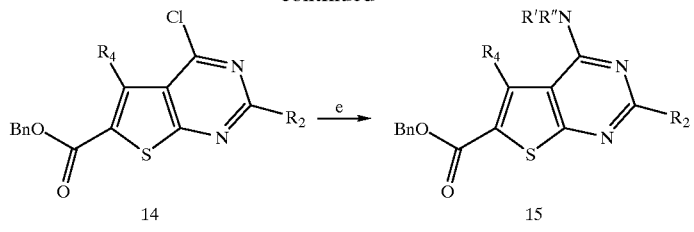

R₃ = H a) EDC, DMF, HOBt
b) HNR³ᵃR³ᵇ
c) H₂NR³ᵃ, neat 120° C.
d) POCl₃
e) NR'R", heat Similar techniques can be used in the pyrrole series. Thus, a pyrrole analog of compound 7 (i.e., instead of compound 7, the corresponding tetrasubstituted pyrrole compound) can be converted to a variety of compounds of Formula II, e.g., as described above and in Example 18, infra.

EXAMPLE 2

Preparation of 3(1,1-Dimethylethyl) 5-benzyl 2-amino-4-methylthiophene-3,5-dicarboxylate To a suspension of benzyl acetoacetate (20.0 g, 104.1 mmol), t-butyl cyanoacetate (14.7 g, 104.1 mmol), sulfur (3.5 g, 109.3 mmol) and pyridine (120 ml) was added diethyl amine dropwise. After 2 days, the black solution was concentrated under reduced pressure, dissolved in Et₂O and filtered through silica. The eluent was then concentrated. Chromatography (silica, 7:1 hexane/EtOAc) yielded 25.58 g (71%) of a orange oil which slowly crystallized upon standing. $^1$H-NMR (CDCl₃) 1.58 (s. 9H), 2.70 (s, 3H), 5.27 (s, 2H), 7.38 (m, 5H).

EXAMPLE 3

Preparation of 2-Amino-4-methylthiophene-3,5-dicarboxylic acid 3-(1,1-Dimethylethyl) ester To a cold degassed solution of the compound prepared in Example 2 (22.6 g, 64.9 mmol) in EtOH (700 ml) was added 3M KOH (350 ml) dropwise over 30 minutes. When the addition was complete the reaction was warmed to room temperature. After 3 days the reaction was diluted with H₂O, Et₂O and brine. The layers were separated and the aqueous layer was further extracted with Et₂O (2x). The combined Et₂O layers were extracted with 0.1M KOH (1x). All of the aqueous basic layers were combined and cooled to 15° C. and acidified dropwise with 3M HCl (aq) (note: do not let the internal temperature rise above 18° C.).

The flask was cooled to 5° C. After 30 minutes at 5° C., crystals (11.80 g, 71%) which formed were filtered and washed with cold water. $^1$H-NMR (CDCl₃) 1.58 (s, 9H), 2.23 (s, 3H), 5.83 (brs, 1H), 5.98 (brs, 2H); mp=136–137° C.

EXAMPLE 4

Preparation of 2-(((4-methylphenyl)sulfonyl)amino)-4-methylthiophene-3,5-dicarboxylic acid 3-(1,1-Dimethylethyl) ester To a solution of the compound prepared in Example 3 (1.0 g, 3.89 mmol) in DCM (22 ml) and pyridine (2 ml) was added p-toluenesulfonyl chloride. After 3 days, the reaction solution was diluted with 0.1N HCl and the layers were separated. The organic layer was washed sequentially with 0.1N HCl (1x) and H₂O (2x), dried over MgSO₄, filtered and concentrated under reduced pressure. The crude oil was filtered through silica and yielded 1.50 g (94%) of a brown viscous oil. $^1$H-NMR (CDCl₃) 1.50 (s, 9H), 2.22 (s, 3H), 2.37 (s, 3H), 6.26 (s, 1H), 7.24 (d, 2H, J=8.8 Hz), 7.80 (d, 2H, J–8.8 Hz), 10.57 (brs, 1H).

EXAMPLE 5

Preparation of 3-(1,1-Dimethylethyl) 5-benzyl 2-(((trifluoromethyl)carbonyl)amino)-4-methylthiophene-3,5-dicarboxylate The compound prepared in Example 2 (20.5 g, 59 mmol) was dissolved in DCM (200 ml) and pyridine (5.25 ml, 65 mmol). Trifluoroacetic anhydride (13.0 g, 62.0 mmol) was added dropwise. After 1 day, the reaction solution was diluted with H₂O and DCM. The layers were separated and the aqueous layer was extracted with DCM (2x). The combined organic layers were dried over MgSO₄, filtered and concentrated. The crude solid was recrystallized from EtOH/H₂O to yield 20.3 g of off white crystals. $^1$H-NMR (CDCl₃) 1.62 (s, 9H), 2.76 (s, 3H), 5.32 (s, 2H), 7.41 (m, 5H); $^{13}$C-NMR (CDCl₃) 15.5 (CH₃), 28.2 (CH₃), 65.5 (CH₂), 84.2 (C), 117.8 (C,q, J=286 Hz), 118.2 (C), 119.5 (C), 128.1 (CH), 128.3 (CH), 128.7 (CH), 135.7 (C), 145.3 (C), 149.1 (C), 154.3 (C, q, J=40 Hz), 162.3 (C), 165.0 (C); mp=136–138° C.

EXAMPLE 6

Preparation of 2-(((Trifluoromethyl)carbonyl)amino)4-methylthiophene-3,5-dicarboxylic acid 5-benzyl ester The compound prepared in Example 5 (155 mg, 0.34 mmol) was dissolved in DCM (2.5 ml) and TFA (3 ml) was added dropwise. After 18 h, the reaction was concentrated. The crude solid was partitioned between CHCl₃ and H₂O. The layers were separated and the aqueous layer was extracted with CHCl₃ (2x). The combined organic layers were dried over MgSO₄, filtered and concentrated to yield 130 mg of a white solid (99%). $^1$H-NMR (CDCl₃) 2.83 (s, 3H), 5.34 (s, 2H), 7.40 (m, 5H); $^{13}$C-NMR (CDCl₃); mp–179–183° C.

EXAMPLE 7

Preparation of 2-Amino-4-methylthiophene-3,5-dicarboxylic acid 5-benzyl ester

The compound prepared in Example 6 was dissolved in THF (1 ml) and Et₂O (1 ml). 10% Na₂CO₃ (2 ml) was added and the reaction was stirred vigorously. After 24 h, the reaction was acidified with 1M HCl and extracted with CHCl$_3$ (2×). The combined organic layers were dried over MgSO$_4$, filtered and concentrated to yield 40 mg of a white solid (96%). $^1$H-NMR (CDCl$_3$) 2.83 (s, 3H), 5.34 (s, 2H), 7.40 (m, 5H); $^{13}$C-NMR. (d6-DMSO) 15.7 (CH$_3$), 65.1 (CH$_2$), 105.3 (C), 107.0 (C), 127.7 (CH), 128.0 (CH), 128.6 (CH), 136.6 (C), 148.7 (C), 161.9 (C), 166.7 (C), 167.2 (C);

EXAMPLE 8

Preparation of 3-(1,1-Dimethylethyl) 5-benzyl 2-(((phenyl)carbonyl)amino)-4-methylthiophene-3,5-dicarboxylate To a solution of the compound prepared in Example 2 (2.78 g, 8.00 mmol), pyridine (1.6 ml, 20 mmol) and DCM (35 ml) was added benzoyl chloride (1.18 g, 8.40 mmol) dropwise. After 18 hours, the reaction was diluted reaction with EtOH and stirred for 1 hour. The reaction solution was diluted with DCM and H$_2$O. The layers were separated and the aqueous layer was extracted with DCM. The combined aqueous layers were washed with H$_2$O (2×), dried over MgSO$_4$ and concentrated under reduced pressure. Recrystallization (hexane/EtOAc) yields 3.01 g (83%) of a tan solid. $^1$H-NMR(CDCl$_3$) 1.56 (s, 9H), 2.79 (s, 3H), 5.32 (s, 2H), 7.30–7.60 (m, 8H), 8.03 (d, 2H, J=8.0 Hz); mp=134–135° C.

EXAMPLE 9

Preparation of 3-(1,1-Dimethylethyl) 5-benzyl 2-(((3-pyridyl)carbonyl)amino)-4-methylthiophene-3,5-dicarboxylate The title compound was prepared by following the procedure of Example 8, using nicotinoyl chloride in place of benzoyl chloride. Yield: (71%). $^1$H-NMR (CDCl$_3$) 1.62 (s, 9H), 2.79 (s. 3H), 5.35 (s, 2H), 7.30–7.60 (m, 6H), 8.35 (m, 1H), 8.84 (brs, 1H), 9.28 (brs, 1H); mp=165–166° C.

EXAMPLE 10

Preparation of 3-(1,1-Dimethylethyl) 5-benzyl 2-((methylcarbonyl)amino)-4-methylthiophene-3,5 dicarboxylate The title compound was prepared by following the procedure of Example 7, using acetyl chloride in place of benzoyl chloride. Yield: (80%). $^1$H-NMR (CDCl$_3$) 1.60 (s, 9H), 2.30 (s, 3H), 2.74 (s, 3H), 5.29 (s, 2H), 7.30–7.50 (m, 5H); mp=157–158° C.

EXAMPLE 11

Preparation of 2-((methylcarbonyl)amino)-4-methylthiophene-3,5-dicarboxylic acid 3-(1,1-Dimethylethyl) ester To a solution of the compound prepared in Example 10 (1.10 g, 2.84 mmol) in EtOAc (225 ml) was added Pd(OH)$_2$ (0.50 g, 0.47 mmol). The flask was then flushed with H$_2$. After 1 day, the reaction was purged with N$_2$ and filtered. The catalyst was washed with hot EtOH (2×). The combined filtrates were concentrated under reduced pressure; to yield 810 mg of a tan solid (95%). $^1$H-NMR (CDCl$_3$) 1.60 (s, 9H), 2.30 (s, 3H), 2.74 (s, 3H), 5.29 (s, 2H), 7.30–7.50 (m, 5H). 1.56 (s, 9H), 2.25 (s, 3H), 2.67 (s, 3H), 5.60 (brs, 2H) 11.40 (brs, 1H).

EXAMPLE 12

Preparation of 2-(((3-pyridyl)carbonyl)amino)-4-methylthiophene-3,5 dicarboxylic acid 3-1,1-Dimethylethyl) ester The title compound was prepared from the compound prepared in Example 9, following the procedure of Example 11. Yield: (78%). $^1$H-NMR (CDCl$_3$) 1.54 (s, 9H), 2.66 (s, 3H), 7.49 (m, 1H), 8.26 (d, 7.3 Hz), 8.75 (m, 1H), 9.18 (m, 1H).

EXAMPLE 13

Preparation of 2-((phenylcarbonyl)amino)-4-methylthiophene-3, 5-dicarboxylic acid 5-benzyl ester To a solution of the compound prepared in Example 8 (1.33 g, 2.94 mmol) in DCM (20 ml). was added TFA (20 ml) dropwise. After 19 hours, the reaction was concentrated under reduced pressure, and partitioned between CHCl$_3$ and H$_2$O. The aqueous phase basified with sat. NaHCO$_3$, and the layers were separated. The aqueous phase was extracted with CHCl$_3$. The combined organic layers were washed with H$_2$O, dried over MgSO$_4$ and concentrated under reduced pressure to yield 1.10 g (95%) of a tan solid. $^1$H-NMR (CDCl$_3$) 2.76 (s, 3H) 5.23 (s, 2H), 7.20–7.60 (m, 8H), 7.93 (d, 2H, J=8.0 Hz)

EXAMPLE 14

Preparation of 3-(1,1-Dimethylethyl)-5-(1-hydroxysuccinimide) 2-(((phenyl) -carbonyl) amino)-4-methylthiophene-3,5-dicarboxylate To a solution of 2-((phenylcarbonyl)amino)-4-methylthiophene-3,5-dicarboxylic acid 3-(1,1-Dimethylethyl) ester (180 mg, 0.50 mmol) in DCM (5 ml) was added EDC (143 mg, 0.75 mmol), and TEA ( 75 mg, 0.75 mmol). After 1 hour the N-hydroxysuccinimide (87 mg, 0.75 mmol) was added. After 5 hours, the reaction was diluted with H$_2$O and the layers were separated. The aqueous layer was extracted with DCM. The combined DCM layers were dried over MgSO$_4$ and concentrated under reduced pressure. The solid was dissolved in 3:1 hexane/EtOAc and filtered through silica. The eluent was collected and concerned under reduced pressure to yield 173 mg of a tan solid (76%). $^1$H-NMR (CDCl$_3$) 1.65 (s, 9H) 2.77 (s, 3H), 2.89 (s, 4H), 5.30 (s, 2H), 7.60 (m, 3H), 8.04 (dd, 2H, J=1.8, 7.9 Hz).

EXAMPLE 15

5-Benzyl 4-keto-3-methyl-6-phenythiophene-5,7-oxazine-5 carboxylate

To a solution of the compound prepared in Example 13 (1.10 g, 2.78 mmol) in DCM (50 ml) was added EDC (0.8 g, 4.17 mmol), HOBt (639 mg, 4.17 mmol) and catalytic DMAP. After 20 hours, the reaction solution was diluted with DCM and H$_2$O. The layers were separated and the aqueous layer was extracted with DCM. The combined organic layers were dried over MgSO$_4$ and concentrated under reduced pressure. The crude solid was dissolved in Hexane/EtOAc (1:1) and filtered through silica to yield 1.08 g (98%) of an off white solid. $^1$H-NMR (CDCl$_3$) 2.91 (s, 9H), 5.38 (s, 2H). 7.30–7.60 (m, 8H). 8.34 (dd, 2H, J=1.3, 8.2 Hz).

Solid-Phase Synthesis

Solid phase synthesis of the compounds of the invention can be accomplished as depicted in the illustrative synthesis of Scheme 5.

Scheme 5

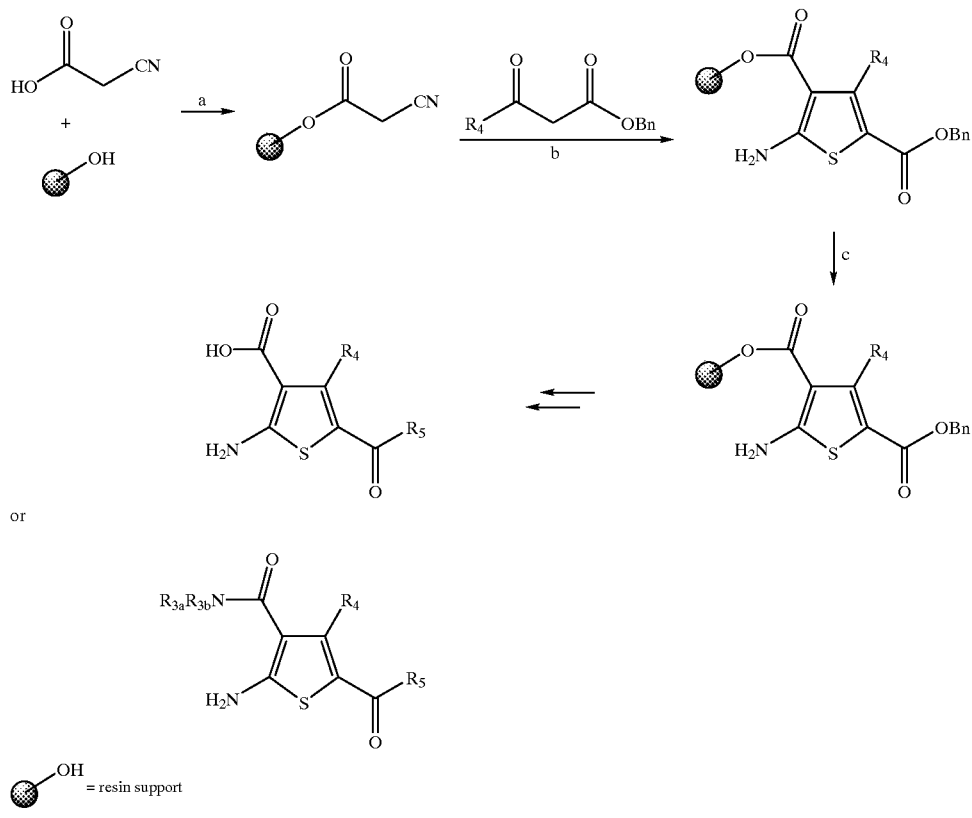

a) BOP, Et₃N, DCM
b) S, Et₃N or Et₂NH, pyr
c) R²COCl or (R²SO₂)₂O, DCM

An exemplary synthesis was performed as described in Example 16.

EXAMPLE 16

Preparation of 2-(((1-methylethyl)carbonyl)amino)-4-methylthiophene-3,5,-dicarboxylic acid 5-benzyl ester Wang resin (1.0 g; 1.0 mmole/g) was suspended in DCM (5 ml). Cyanoacetic acid (340 mg, 4.0 mmol), BOP (1.77 g, 4.0 mmol) and triethylamine (404 mg, 4.0 mmol) were added sequentially. The heterogeneous reaction mixture was shaken at room temperature. After 3 days, the reaction mixture was filtered and the resin was washed with DMF (2×), 85% isopropanol (aq.) (2×), DMF (2×) and DCM (2×) and air dried to yield 1.10 g of tan resin. A portion of the resin (400 mg), 0.36 mmol) was suspended in pyridine(4 ml) and benzyl acetoacetate (384 mg, 2.0 mmol), sulfur (128 mg, 4.0 mmol) and diethylamine (59 mg, 0.8 mmol) were added. The reaction mixture was shaken at room temperature. After 4 days, the heterogeneous reaction mixture was filtered and the resin was washed with DMF (3×) and DCM (2×). The resulting reddish resin (480 mg, 0.36 mmol) was suspended in DCM (4 ml). Pyridine (316 mg, 4.0 mmol) and isobutyryl chloride (467 mg, 4.4 mmol) were added. The reaction was shaken at room temperature. After 2 days, the reaction was filtered and the resin was washed with DCM, DMF (2×), 50% DMF (aq.) (2×), DMF (2×) and DCM (2×) to yield 490 mg of resin. The thiophene was cleaved by treating the resin (200 mg, 0.18 mmol) with 95% TFA, 5% DCM and catalytic $H_2O$. After 3 hours of shaking the reaction was filtered, and the reaction washed with DCM (2×). The combined filtrates were concentrated under reduced pressure to yield 40 mg of a crude solid. $^1$H-NMR (CDCl₃) 1.31 (d, 6H, J=7.0 Hz), 2.69 (m, 1H), 2.83 (s, 3H), 7.40 (m, 5H), 11.44 (brs, 1H).

EXAMPLE 17

Library Synthesis

A library of thiophene compounds was synthesized with the use of an automated workstation as follows:

To provide a library of compounds, variegated populations of starting materials were provided. Thus, the starting material $R_4C(O)CH_2R_5$ was provided as a variegated population comprising three compounds, in which $R_4$ was methyl, benzyl, or —$CH_2OCH_3$ (for all compounds $R_5$ was —C(O)OBn, in which Bn is benzyl). These three compounds were reacted with t-butyl cyanoacetate and sulfur, in the presence of pyridine as described herein, to provide three thiophene compounds (e.g., compounds of Formula Ia in which $R_{2a}$ and $R_{2b}$ are both hydrogen, $R_3$ is —C(O)OtBu, $R_5$ is —C(O)OBn, and $R_4$ is methyl, benzyl, or —$CH_2OCH_3$. These syntheses were performed on 50 g scale in yields of 69–72%.

Thirty reaction vessels were charged with pyridine and with one of the three thiophene compounds (e.g., as described above, in which R₄ is methyl, benzyl, or —CH₂OCH₃). To each reaction vessel was added an acylating agent (i.e., an acid chloride or sulfonyl anhydride selected from a group of 10 acid chlorides and anhydrides). When reaction was complete (yields 66–83%), each vessel contained one of a library of thirty thiophenes of Formula Ia, differing in the substituents at R₄ (as described above) and at R$_{2a}$ (i.e., R$_{2a}$ is one of 10 different acyl or sulfonyl groups). These compounds were then amidated as described below.

Further library diversification was achieved by selective deprotection of the carboxyl protecting groups (i.e., -tBu or Bn). The benzyl group was removed by hydrogenolysis or selective hydrolysis, while the t-butyl group could be removed by treatment with TFA.

In the event, the carboxy group at R₅ was deprotected by hydrogenolysis, and converted to the N-hydroxysuccinimide active ester by standard methods. For the amidation reactions, an automated workstation (Hewlett-Packard PrepStation) was used, according to the manufacturer's instructions, to manipulate the reactants. The workstation dispensed an aliquot of an active NHS ester of a thiophene compound into each of 80 reaction vials and then one of 80 different amines was added to each reaction vial. Upon completion of the reaction, a library of thiophene compounds of Formula I was formed; the workstation then performed an aqueous workup of the reactions. The compounds of the library, varied in the substituent at R₅ (i.e., R$_{5'}$ is —OBn or NR₈R₉, in which R₈ and R₉ are each independently hydrogen, alkyl, aryl, or heterocyclyl, or R₈ and R₉ together with the nitrogen atom to which they are attached, form a 3- to 8-membered heterocyclic ring). By using the variety of acylated (or sulfonated) compounds prepared as described above, thousands of different thiophene compounds were prepared.

An automated preparation of acylated (or sulfonated) compounds can be performed as follows:

A workstation is set up to perform parallel synthesis according to the manufacturer's instructions. Thirty reaction vessels are charged with pyridine and with one of the three thiophene compounds (e.g., as described above, in which R₄ is methyl, benzyl, or —CH₂OCH₃), and the workstation is programmed to supply to each reaction vessel an acylating agent (e.g., an acid chloride, sulfonyl chloride or sulfonyl anhydride selected from a group of acid chlorides and anhydrides). When reaction is complete, after workup each vessel contains one of a library of thirty thiophenes of Formula I, differing in the substituents at R₄ (as described above) and at R$_{2a}$ (i.e., R$_{2a}$ is one of 10 different acyl or sulfonyl groups).

Thus, a library having at least 4800 compounds as members (i.e., one of 10 substituents at R$_{2a}$, one of two substituents at R₃ (—OH or —OtBu), one of three substituents at R₄, and one of 80 substituents at R₅,) can be provided by the methods of the invention. Further library diversification can be obtained, if desired, by derivatizing (e.g., amidating) the R₃ carboxy group, e.g., as described for R₅, supra.

EXAMPLE 18

Synthesis of Fused Heterocycles

Compounds of Formula I can be used to prepare other compounds of the invention, e.g., compounds of Formula II. Thus, for example, compounds of Formula I can be converted into compounds of Formula II as described herein and/or as shown in Scheme 6, below.

Scheme 6

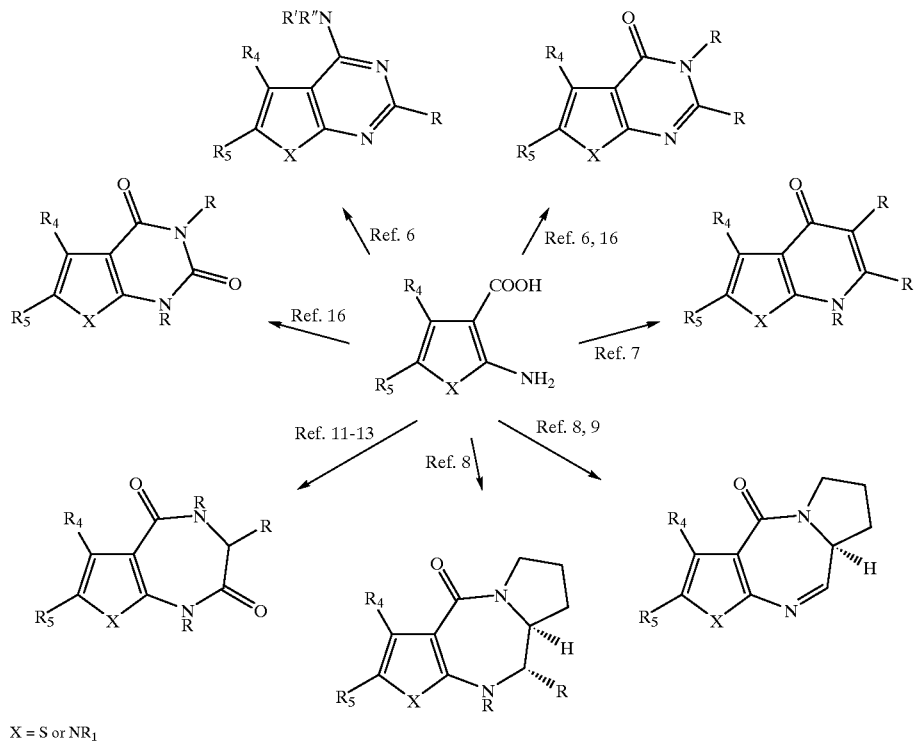

X = S or NR₁

In Scheme 6, $R_1$, $R_4$, and $R_5$ have the meanings described supra, and R, R', and R" are, independently for each occurrence, substituents such as hydrogen, alkyl, or aryl.

It will be appreciated from the foregoing that the synthesis of compounds of Formula II from the compounds of Formula I is well within the capabilities of the ordinarily-skilled artisan using no more than routine experimentation, in light of the teachings herein. In particular, references 6–16 describe protocols which, with only routine modifications, can be used to transform compounds of Formula I into a variety of compounds of Formula II.

EXAMPLE 19

Anti-Cancer Activity

To screen compounds of the invention for anti-cancer activity, a screening assay was developed as described below.

In an exemplary assay, small cell lung carcinoma cell lines were employed. Two cell lines were used: N417 and BEAS (acontrol) (others are readily available). N417 is a small cell lung carcinoma (SCLC) variant and BEAS is a virally transformed human lung epithelial line. The cells are cultured in RPMI 1640 (Sigma Chemical Co, St. Louis, Mo.) with 5% FBS. On day 1 of the assay cells are harvested, resuspended in PBS and triturated to break up clumps for counting. After counting, the cells are resuspended in a medium of RPMI containing 5 ng/ml sodium selenite, 5 μg/ml insulin and 5 μg/ml transferin additives with no serum. The cells are plated at 50,000 cells per well in 200 μl final volume in 96 well plates and allowed to rest overnight in a humidified $CO_2$ containing incubator. Test compounds and controls are added to the wells on the second day. The test compounds are added to a final concentration of 10 μM. The controls include 100 μM etoposide, 50 μM peptidic substance P derivative D (i.e., D-Arg -Pro-Lys-Pro-D-Phe-Gln-D-Trp-Phe-D-Trp-Leu-Leu-$NH_2$) and the compound diluent 1.13% DMSO. The cultures are returned to the incubator for 36 to 48 hours. On day 4, the viability of the cultures is determined using the MTT assay (Mosmann, T., *J. Immunol. Methods* 65:55 (1983)). MTT is a tetrazolium salt that is used to indicate the reducing capacity of cellular mitochondria. After incubation for 4 hours with MTT, the reduced MTT is converted to a colorimetric product using an acidified isopropanol solution. The absorption of the wells is read at 540 nm with a reference wavelength of 650 nm. The MTT OD readings are linearly related to the number of cells in a well. The percent viability is determined by dividing the MTT OD reading for a test compound to the MTT OD reading for the solvent control. A compound is considered to have anti-cancer activity if the viability of the N417 SCLC is 25% or less and the viability of the control BEAS cell is greater than 75%.

Using the above-described assay, compounds of the invention (prepared as a library by the method described in Example 17, supra) were screened (only a portion of the library described in Example 17 was screened). Examples of results with active compounds are as follows (results were obtained from triplicate experiments):

TABLE 1

Activity of Selected Compounds of the Invention

| Compound | Cell Type | Experiment 1 | Experiment 2 | Experiment 3 |
|---|---|---|---|---|
| 16 | BEAS | 123 | 129 | 104 |
|  | N417 | 25 | 29 | 10 |
| 17 | BEAS | 138 | 158 | 95 |
|  | N417 | 26 | 29 | 10 |
| 18 | BEAS | 91 | 125 | 80 |
|  | N417 | 24 | 26 | 26 |

As the results show, compounds 16, 17, and 18 (structures are shown below) have considerable activity against the SCLC cell line, while having little or no harmful effect on the control cell line.

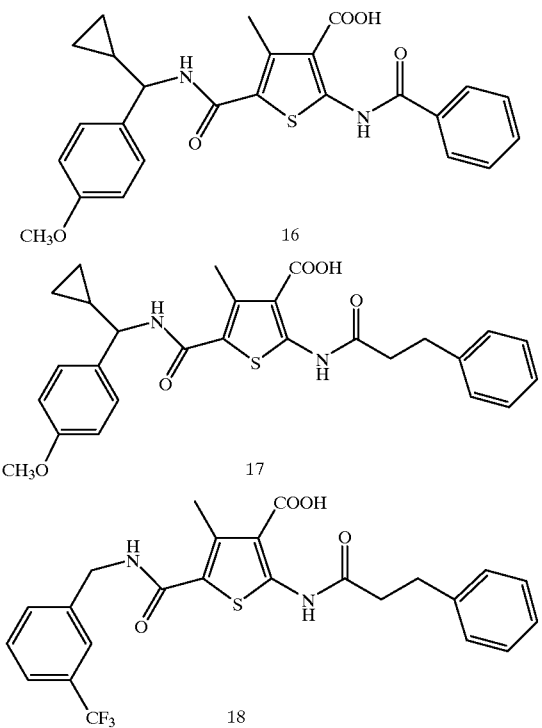

REFERENCES

1. Gewald, K, E. Schinke, and H. Bottcher, *Chem Ber.*, 1966. 99, 94.
2. Sampson, N. and P. Bartlett, *J. Org Chem*, 1991. 56, 7179
3. Greene, T. and P. Wuts, *Protective Groups in Organic Synthesis* Second Edition, 1991, New York: John Wiley and Sons.
4. Errede, L, H. Oien, and D. Yarian, *J. Org. Chem.*, 1977. 42, 12.
5. Roth, H. and K. Eger, *Arch. Pharm.*, 1975. 308. 179.
6. Muller, C., et al., *J. Med Chem.* 1996 39, 2482.
7. Mitscher, L., et al, *J. Med Chem.*, 1978. 21, 485.
8. Wright, W., 1976: U.S. Pat. No. 3,947,408.
9. Carabateas, P.,. 1973: U.S. Pat. No. 3,732,212.
10. Takashi, M., T. Onizawa, and R. Shioda, *Nippon Kagaku Kaishi*, 1972. 8, 1259.
11. Kim, D., *J. Heterocyclic Chem.*, 1975, 12, 1323.
12. Kim, D., .1975: U.S. Pat. No. 3,925,361.
13. Kim, D., .1975: U.S. Pat. No. 3,904,603.

14. Carabateas, P. and L. Harris, *J. Med Chem,* 1966. 9, 6.
15. Mayer, I., et al, *Tetrahedron Lett.,* 1996, 37, 8081.
16. Foster, C. and E. Elam, *J. Org. Chem,* 1976, 41, 2646
17. Molina, P., M. Alajarian, and A. Vidal, *Tetrahedron Lett.,* 1988, 29, 3849.

Those skilled in the art will recognize, or be able to ascertain using no more than routine experimentation, numerous equivalents to the specific procedures described herein. Such equivalents are considered to be within the scope of this invention and are covered by the following claims.

The contents of all publications and patent applications cited herein are hereby incorporated by reference.

Other embodiments are within the following claims.

What is claimed is:

1. A compound represented by the formula (Formula Ia):

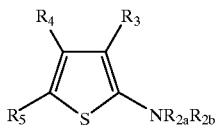

in which $R_{2a}$ and $R_{2b}$ are each, independently, hydrogen, alkyl, aryl, alkylcarbonyl, arylcarbonyl, alkoxycarbonyl, aryloxycarbonyl, aminocarbonyl, alkylsulfonyl, or arylsulfonyl; or $R_{2a}$ and $R_{2b}$ taken together with the nitrogen atom to which they are attached, form a 3- to 8-membered ring;

$R_3$ is hydrogen, —CN or —C(O)$R_6$;

$R_4$ is alkyl, aralkyl or aryl;

$R_5$ is hydrogen, halogen, alkyl, aryl, or —C(O)$R_{5'}$; and $R_{5'}$ and $R_6$ are each independently hydroxyl, alkyl, aryl, alkoxy, aryloxy, —SH, alkylthio, arylthio, amino, or a linker to a solid support;

or a salt thereof, with the proviso that $R_{2a}$ and $R_{2b}$ are not hydrogen simultaneously.

2. The compound of claim 1, wherein $R_{2b}$ is arylcarbonyl.
3. The compound of claim 1, wherein $R_6$ is hydroxy.
4. The compound of claim 1, wherein $R_6$ is a linker to a solid support.
5. The compound of claim 1, wherein $R_4$ is methyl.
6. The compound of claim 1, wherein $R_5$, is amino.
7. A compound represented by the formula (Formula Ib):

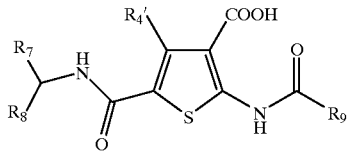

in which $R_4$ is alkyl;
$R_7$ is hydrogen alkyl; orcycloalky
$R_8$ is aryl; and
$R_9$ is alkyl or aryl;
or a salt thereof.

8. The compound of claim 7, in which $R_7$ is cyclopropyl.
9. The compound of claim 7, in which $R_9$ is substituted or unsubstituted phenyl.
10. A method for preparing a compound represented by the formula (Formula Ia):

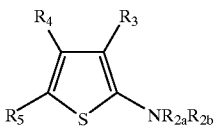

in which $R_{2a}$ and $R_{2b}$ are each, independently hydrogen, alkyl, aryl, alkylcarbonyl, arylcarbonyl, alkoxycarbonyl, aryloxycarbonyl, aminocarbonyl, alkylsulfonyl, or arylsulfonyl; or $R_{2a}$ and $R_{2b}$ taken together with the nitrogen atom to which they are attached, form a 3to 8-membered ring;

$R_3$ is hydrogen, —CN or —C(O)$R_6$;

$R_4$ is alkyl, aralkyl or aryl;

$R_5$ is hydrogen, halogen, alkyl, aryl, or —C(O)$R_{5'}$; and $R_{5'}$ and $R_6$ are each independently hydroxyl, alkyl, aryl, alkoxy, aryloxy, —SH, alkylthio, arylthio, amino, or a linker to a solid support;

or a salt thereof;

the method comprising the step of reacting a first compound represented by the formula $R_4C(O)CH_2R_5$ with a compound represented by the formula $R_6C(O)CH_2CN$, and with elemental sulfur, in the presence of a pyridine compound, such that a compound of Formula Ia is prepared.

11. The method of claim 10, in which $R_3$ is —C(O)$R_6$.
12. The method of claim 11, in which at least about 1–2 moles of sulfur are used for each mole of $R_4C(O)CH_2R_5$.
13. The method of claim 11, in which the compound represented by the formula $R_6C(O)CH_2CN$ is t-butylcyanoacetate.
14. The method of claim 11, in which $R_{2a}$ is hydrogen.
15. The method of claim 11, in which at least one of $R_{5'}$, and $R_6$ is a linker to a solid support, and the compound of Formula Ia is prepared by solid-phase synthesis.
16. The method of claim 11, in which the method includes the further step of purifying the compound of Formula Ia.
17. The method of claim 11, in which the reaction is performed in a solvent comprising pyridine.
18. The method of claim 17, in which the solvent comprises at least about 50% pyridine.
19. A library of compounds as claimed in claim 1, wherein the library comprises a multiplicity of compounds represented by the formula (Formula Ia).
20. The library of claim 19, in which the library comprises at least 30 different compounds.
21. The method of claim 10, wherein at least one of said first and second compounds is provided as a variegated population such that a library of compounds of Formula Ia is prepared.
22. A method for inhibiting unwanted cell growth in a subject, the method comprising: administering to the subject an effective amount of a compound represented by the formula (Formula Ia):

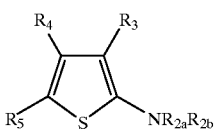

in which $R_{2a}$ and $R_{2b}$ are each, independently selected from the group consisting of hydrogen, alkyl, aryl, alkylcarbonyl, arylcarbonyl, alkoxycarbonyl, aryloxycarbonyl, aminocarbonyl, alkylsulfonyl, or arylsulfonyl; or $R_{2a}$ and $R_{2b}$ taken together with the nitrogen atom to which they are attached, form a 3- or 8-membered ring;

$R_3$ is hydrogen, —CN or —C(O)$R_6$;

$R_4$ is alkyl, aralkyl or aryl;

$R_5$ is hydrogen, halogen, alkyl, aryl, or —C(O)$R_5$; and $R_{5'}$ and $R_6$ are each independently selected from the group consisting of hydroxy, alkyl, aryl, alkoxy, aryloxy, —SH, alkylthio, arylthio, amino, or a salt thereof;

such that unwanted cell growth is inhibited in the subject.

23. The method of claim 22, in which the unwanted cell growth is due to lung cancer.

24. The method of claim 22, wherein said compound of Formula Ia is represented by the formula (Formula Ib):

in which $R_{4'}$ is alkyl;

$R_7$ is hydrogen or alkyl; $R_8$ is aryl; and $R_9$ is alkyl or aryl;

or a salt thereof.

25. A pharmaceutical composition comprising a compound of claim 1 in a pharmaceutically-acceptable carrier.

26. A compound represented by the formula (Formula Ia):

in which $R_{2a}$ is hydrogen, alkyl, aryl, alkylcarbonyl, arylcarbonyl, alkoxycarbonyl, aryloxycarbonyl, aminocarbonyl, alkylsulfonyl, or arylsulfonyl;

$R_{2b}$ is arylcarbonyl;

$R_3$ is hydrogen, —CN or —C(O)$R_6$;

$R_4$ is alkyl, aralkyl or aryl;

$R_5$ is hydrogen, halogen, alkyl, aryl, or —C(O)$R_5$; and $R_{5'}$ and $R_6$ are each independently hydroxyl, alkyl, aryl, alkoxy, aryloxy, —SH, alkylthio, arylthio, amino, or a linker to a solid support;

or a salt thereof.

27. A library of compounds as claimed in claim 1, wherein said library comprises a multiplicity of compounds represented by the Formula Ia, said library having been prepared by the method comprising:

reacting a first compound represented by the formula $R_4C(O)CH_2R_5$ with a second compound represented by the formula $R_6C(O)CH_2CN$, and with elemental sulfur, in the presence of a pyridine compound, in which at least one of said first and second compounds is provided as a variegated population, such that a library of compounds of Formula Ia is prepared.

28. A method for preparing a library of compounds represented by the formula (Formula Ia):

in which $R_{2a}$ and $R_{2b}$ are each, independently hydrogen, alkyl, aryl, alkylcarbonyl, arylcarbonyl, alkoxycarbonyl, aryloxycarbonyl, aminocarbonyl, alkylsulfonyl, or arylsulfonyl; or $R_{2a}$ and $R_{2b}$ taken together with the nitrogen atom to which they are attached, form a 3to 8-membered ring;

$R_3$ is hydrogen, —CN or —C(O)$R_6$;

$R_4$ is alkyl, aralkyl or aryl;

$R_5$ is hydrogen, halogen, alkyl, aryl, or —C(O)$R_5$; and $R_{5'}$ and $R_6$ are each independently hydroxyl, alkyl, aryl, alkoxy, aryloxy, —SH, alkylthio, arylthio, amino, or a linker to a solid support;

or a salt thereof;

the method comprising the step of reacting a first compound represented by the formula $R_4C(O)CH_2R_5$ with a second compound represented by the formula $R_6C(O)CH_2CN$, and with elemental sulfur, in the presence of a pyridine compound, wherein at least one of said first and second compounds is provided as a variegated population such that a library of compounds of Formula Ia is prepared.

29. The compound of claim 1 represented by the formula (Formula Id):

in which $R_{2a}$ is optionally substituted arylsulfonyl or optionally substituted arylcarbonyl;

$R_{5'}$ is hydroxy or alkoxy;

$R_6$ is alkoxy;

or a salt thereof.

30. The compound of claim 29 wherein $R_{2a}$ is a substituted arylsulfonyl.

31. The compound of claim 30 wherein the aryl moiety of said arylsulfonyl is disubstituted with halogen.

32. The compound of claim 31 wherein the halogen is chlorine.

33. The compound of claim 30 wherein the aryl moiety of said arylsulfonyl is disubstituted with trifluoromethyl.

34. The compound of claim 29 wherein $R_{2a}$ is a monosubstituted arylsulfonyl.

35. The compound of claim 34 wherein the aryl moiety of said arylsulfonyl is monosubstituted with halogen.

36. The compound of claim 35 wherein the halogen is chlorine.

37. The compound of claim 30 wherein $R_{5'}$ and $R_6$ are ethoxy.

38. The compound of claim 30 wherein $R_{5'}$ is hydroxy and $R_6$ is ethoxy.

39. The compound of claim 30 wherein $R_{5'}$ and $R_6$ are isopropoxy.

40. The compound of claim 34 wherein $R_{5'}$ and $R_6$ are ethoxy.

41. The compound of claim 33 wherein $R_{5'}$ and $R_6$ are ethoxy.

42. The compound of claim 29 wherein $R_{2a}$ is a substituted arylcarbonyl.

43. The compound of claim 42 wherein the aryl moiety of said arylcarbonyl is disubstituted with halogen.

44. The compound of claim 43 wherein the halogen is chlorine.

45. The compound of claim 42 wherein $R_{5'}$ and $R_6$ are ethoxy.

46. The compound of claim 29 wherein $R_{2a}$ is substituted arylsulfonyl, $R_{5'}$ is hydroxy or alkoxy, and $R_6$ is alkoxy.

47. The compound of claim 46 wherein $R_{2a}$ is phenylsulfonyl, the phenyl moiety of which is disubstituted with chlorine.

48. The compound of claim 47 wherein $R_{5'}$ and $R_6$ are ethoxy.

49. The compound of claim 47 wherein $R_{5'}$ is hydroxy and $R_6$ is ethoxy.

50. The compound of claim 47 wherein $R_{5'}$ and $R_6$ are isopropoxy.

51. The compound of claim 46 wherein $R_{2a}$ is phenylsulfonyl, the phenyl moiety of which is disubstituted with trifluoromethyl.

52. The compound of claim 51 wherein $R_{5'}$ and $R_6$ are ethoxy.

53. The compound of claim 29 wherein $R_{2a}$ is monosubstituted arylsulfonyl and $R_{5'}$ and $R_6$ are alkoxy.

54. The compound of claim 33 wherein $R_{2a}$ is phenylsulfonyl, the phenyl moiety of which is monosubstituted by chlorine.

55. The compound of claim 54 wherein $R_{5'}$ and $R_6$ are ethoxy.

56. The compound of claim 29 wherein $R_{2a}$ is substituted arylcarbonyl and $R_{5'}$ and $R_6$ are alkoxy.

57. The compound of claim 56 wherein $R_{2a}$ is phenylcarbonyl, the phenyl moiety of which is disubstituted by chlorine.

58. The compound of claim 57 wherein $R_{5'}$ and $R_6$ are ethoxy.

59. The sodium salt of the compound of claim 48.

60. The sodium salt of the compound of claim 50.

61. The method of claim 22, wherein said compound of Formula Ia is represented by the formula (Formula Id):

$$\begin{array}{c} CH_3 \quad C(O)R_6 \\ \diagup \diagdown \\ R_5'(O)C \quad S \quad NHR_{2a} \end{array}$$

in which $R_{2a}$ is arylsulfonyl or arylcarbonyl;

$R_{5'}$ is hydroxy or alkoxy;

$R_6$ is alkoxy;

or a salt thereof.

62. The method of claims 10 or 28 wherein said pyridine compound is selected from the group consisting of pyridine, substituted pyridines, lutidine, 2,6,-di-t-butylpyridine, fused pyridines, and quinoline.

63. The method of claim 62 wherein said pyridine compound is pyridine.

64. A pharmaceutical composition comprising a compound of claims 7, 26 or 29 and a pharmaceutically-acceptable carrier.

\* \* \* \* \*

UNITED STATES PATENT AND TRADEMARK OFFICE
CERTIFICATE OF CORRECTION

PATENT NO. : 6,037,340
DATED : March 14, 2000
INVENTOR(S) : Arlindo L. Castelhano and Bryan McKibben It is certified that error appears in the above-identified patent and that said Letters Patent is hereby corrected as shown below: ON THE TITLE PAGE Assignee: "Cadus Pharmaceutical Corporation, Tarrytown, N.Y." should read --OSI Pharmaceuticals, Uniondale, N.Y.--

Page 1, Other Publications Reference 10: "*Naturem*" should read --*Nature*-- column 8, line 12: "$R_5$," should read --$R_{5'}$-- column 8, line 26: "$R_5$" should read --$R_{5'}$-- column 10, line 46: "3to" should read --3- to-- column 24, line 57: "<--e----" should read -- <--e---- --
$$R_2=CR_3$$

column 26, line 65: "d|" should read --d|$R_3$=H-- column 37, line 45: "$R_5$" should read --$R_{5'}$-- column 37, line 57: "$R_4$" should read --$R_{4'}$-- column 37, line 58: "hydrogen alkyl; orcycloalky" should read --hydrogen, alkyl or cycloalkyl;-- column 37, line 60: "or aryl;" should read --or optionally substituted aryl;--

UNITED STATES PATENT AND TRADEMARK OFFICE
CERTIFICATE OF CORRECTION

PATENT NO. : 6,037,340        Page 2 of 2
DATED : March 14, 2000
INVENTOR(S) : Arlindo L. Castelhano and Bryan McKibben It is certified that error appears in the above-identified patent and that said Letters Patent is hereby corrected as shown below:

```
column 38, line 14: "3to" should read --3- to--
```

Signed and Sealed this

Eighth Day of May, 2001

Attest:

NICHOLAS P. GODICI

Attesting Officer     Acting Director of the United States Patent and Trademark Office